US00PP18845P3

(12) United States Plant Patent
Freyre

(10) Patent No.: US PP18,845 P3
(45) Date of Patent: May 27, 2008

(54) ***ANAGALLIS* PLANT NAMED 'WILDCAT MANDARIN'**

(50) Latin Name: *Anagallis monelli*
Varietal Denomination: Wildcat Mandarin

(75) Inventor: Rosanna Freyre, Durham, NH (US)

(73) Assignee: University of New Hampshire, Durhan, NH (US)

( * ) Notice: Subject to any disclaimer, the term of this patent is extended or adjusted under 35 U.S.C. 154(b) by 0 days.

(21) Appl. No.: 11/437,314

(22) Filed: May 19, 2006

(65) Prior Publication Data

US 2007/0271646 P1 Nov. 22, 2007

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP15,136 P2 9/2004 Freyre

*Primary Examiner*—Annette H Para
(74) *Attorney, Agent, or Firm*—Devine, Millimet & Branch; Paul C. Remus; Raymond I. Bruttomesso, Jr.

(57) ABSTRACT

A new and distinct cultiva of *Anagallis* plant named 'Wildcat Mandarin,' characterized by its vigorous and outwardly spreading plant habit; freely branching growth habit; numerous single flowers that are bright orange in color with a pink center; and good garden performance.

2 Drawing Sheets

GOVERNMENT SPONSORSHIP

The development of the present invention was funded in part by USDA/Cooperative State Research, Education and Extension Service 01-90015-0420.

Botanical classification/cultivar designation: *Anagallis monelli* cultivar 'Wildcat Mandarin'.

BACKGROUND OF THE INVENTION

The present Invention relates to a new and distinct cultivar of *Anagallis* plant, botanically known as *Anagallis monelli,* previously identified with code number UNH 062-2 and hereinafter referred to by the cultivar name 'Wildcat Mandarin'.

The new *Anagallis* is a product of a planned breeding program conducted by the Inventor in Durham, N.H. The objective of the breeding program is to create new compact *Anagallis* plants with freely and early flowering habit.

The new *Anagallis* originated from a hybridization made by the Inventor on Feb. 28, 2000 between two proprietary selections of *Anagallis monelli,* not patented, identified as code number UNH 950-2, and UNH 924-3. The new *Anagallis* was selected as a single plant from the resulting progeny in Durham, N.H., on the basis of its plant habit and attractive flower coloration.

Asexual reproduction of the new cultivar by terminal vegetative cuttings since Oct. 15, 2000, in Durham, N.H. has shown that the unique features of this new *Anagallis* are stable and reproduced true to type in successive generations.

SUMMARY OF THE INVENTION

Plants of the cultivar 'Wildcat Mandarin' have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Wildcat Mandarin'. These characteristics in combination distinguish 'Wildcat Mandarin' as a new and distinct cultivar:

1. Vigorous and outwardly spreading plant habit.
2. Freely branching growth habit:
3. Numerous single flowers that are bright orange in color, with a pink center.
4. Good garden performance.

In side-by-side comparisons conducted in Durham, N.H., plants of the new *Anagallis* differed from plants of *Anagallis* 'Wildcat Orange' U.S. Plant Pat. No. 15,136, in the following characteristics:

1. Plants of the new *Anagallis* were more upright and vigorous than plants of the cultivar 'Wildcat Orange'.
2. Plants of the new *Anagallis* had larger flowers than plants of the cultivar 'Wildcat Orange'.
3. Plants of the new *Anagallis* had orange flowers that were brighter than plants of the cultivar 'Wildcat Orange' and had a pink center.
4. Plants of the new *Anagallis* had larger leaves than plants of the cultivar 'Wildcat Orange'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Anagallis.*

One photograph comprises a side perspective view of one typical 20-cm container of 'Wildcat Mandarin' with three plants.

The other photograph is a close-up view of typical flowers and leaves of 'Wildcat Mandarin'.

DETAILED BOTANICAL DESCRIPTION

The aforementioned photographs and following observations and measurements describe plants grown in Durham, N.H., in a heated polyethylene-covered greenhouse with 21° C. day/18° C. night set points. After planting rooted cuttings, plants were grown for about four months in 20-cm containers with three plants per container. Color references are made to The Royal Horticultural Society Colour Chart, 1995 Edition, except where general terms of ordinary dictionary significance are used. Color was evaluated under indirect, natural light.

Botanical classification: *Anagallis monelli* cultivar 'Wildcat Mandarin'.

Parentage:

*Female parent.*—Proprietary selection of *Anagallis monelli* identified as code number UNH 950-2, not patented.

*Male parent.*—Proprietary selection of *Anagallis monelli* identified as code number UNH 924-3, not patented.

Propagation:

*Type cutting.*—Terminal vegetative cuttings.

*Time to initiate roots.*—About five days at 21° C.

*Time to develop roots.*—About 15 days at 21° C.

*Root description.*—Fine, fibrous; white, color 155D.

*Rooting habit.*—Freely branching.

Plant description:

*Form.*—Annual flowering plant; vigorous; initially upright, then semi-upright to outwardly spreading and trailing; uniformly mounded plant form. Freely branching habit with lateral branches potentially forming at very node.

*Plant height.*—About 30 cm.

*Plant diameter* (*area of spread*), *single plant.*—About 40 cm.

*Vigor.*—Vigorous; rapid growth rate.

*Lateral branches.*—Length: About 30 cm. Diameter: About 2.5 mm. Internode length: 3–4.5 cm.

*Texture.*—Smooth, glabrous. Color: 144A.

*Foliage description.*—Arrangement: Opposite; towards terminals, in whorls of three; simple; sessile. Length: About 2.5 cm. Width: About 8 mm. Shape: oblong to oblanceolate. Apex: Acute. Base: Truncate. Margin: Entire. Texture, upper and lower surfaces: Glabrous, smooth. Venation pattern: Pinnate. Color: Developing leaves, upper and lower surfaces: 144A. Fully expanded leaves, upper surface: 137A. Fully expanded leaves, lower surface: 137C. Venation, upper surface: 137A. Venation, lower surface: 137C.

Flower description:

*Flower type and habit.*—Single star-shaped flowers; flowers face mostly upward or outward; terminal or axillary; freely flowering habit. 3–4 flowers per node; about 8 open flowers and about 12 flower buds per lateral branch at one time.

*Natural flowering season.*—Plants flower from April to October in the Northern Hemisphere until frost in the autumn; flowering continuous during this period. Plants start flowering about six to eight weeks after planting rooted cuttings. Flowers not persistent.

*Flower longevity on the plant.*—About four to five days.

*Fragrance.*—None detected.

*Flower size.*—Diameter: 2.7–2.9 cm. Depth (height): About 5 mm.

*Flower buds.*—Length: About 7 mm. Diameter: About 4 mm. Shape: Ovate. Color: 34A.

*Petals.*—Quantity/arrangement: Five petals arranged in a single whorl. Length: About 1.7 cm. Width: About 1.7 cm when extended. Shape: Rhomboid, edges curl upwards. Apex: Rounded. Base: Wedged. Margin: With tiny teeth. Texture, upper and lower surfaces: Smooth, velvety. Color: When opening, upper surface: 32A. When opening, lower surface: 34A. Fully opened, upper surface: 33B; base, 67A. Fully opened, lower surface: 33C; base, 67A.

*Sepals.*—Arrangement/appearance: Five sepals arranged in a single whorl between the petals; star-shaped. Length: About 7 mm. Width: About 1.2 mm. Shape: Narrowly lanceolate. Apex: Acute. Base: Truncate. Margin: Entire. Texture, upper and lower surfaces: Smooth, glabrous. Color, upper and lower surfaces: 137A.

*Pedicels.*—Length: About 4.5 cm. Width: About 1 mm. Angle: About 45° from the main stem. Strength: Moderately strong. Texture: Smooth, glabrous. Color: 146B.

*Reproductive organs.*—Stamens: Quantity per flower: Five. Anther shape: Sickle-shaped. Anther length: About 2 mm. Anther width: About 1 mm. Anther color: 12A. Pollen amount: Moderate. Pollen color: 12A. Filament length: About 4 mm. Filament width: About 1 mm. Pistils: Quantity per flower: One. Pistil length: About 7 mm. Style length: About 5 mm. Style color: 67A. Stigma shape: Rounded. Stigma color: 146C. Ovary color: 146C.

*Seed/fruit.*—See and/or fruit production is moderate under open pollination with other *Anagallis* plants. Fruit is a capsule of 0.5 cm diameter which dries upon maturity and has circumscissle dihiscence. Fruits may contain up to 30 small dark brown seeds, 0.8 mm in diameter.

Disease/pest resistance: Plants of the new *Anagallis* have not been noted to be resistant to pathogens or pests common to *Anagallis*.

Garden performance: Plants of the new *Anagallis* have been observed to have good garden performance and tolerate temperatures from −5 to 40° C.

What is claimed is:

1. A new and distinct cultivar of *Anagallis* plant named 'Wildcat Mandarin,' as illustrated and described.

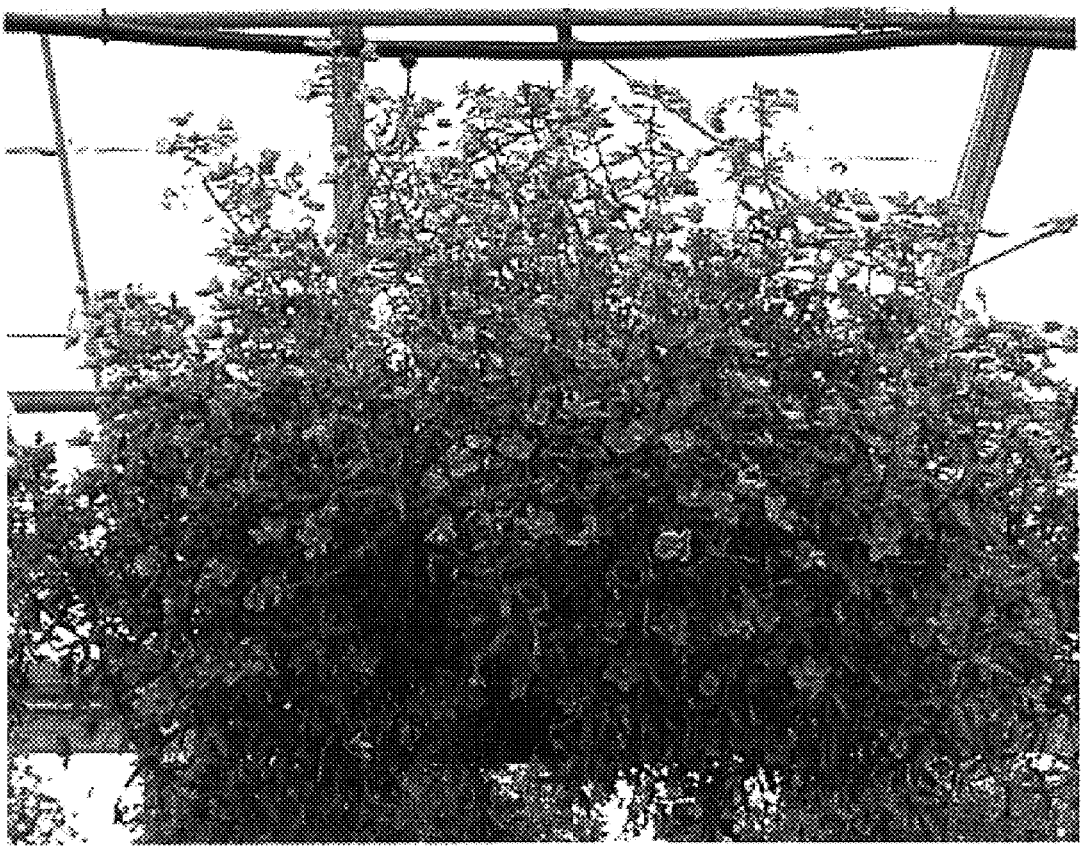

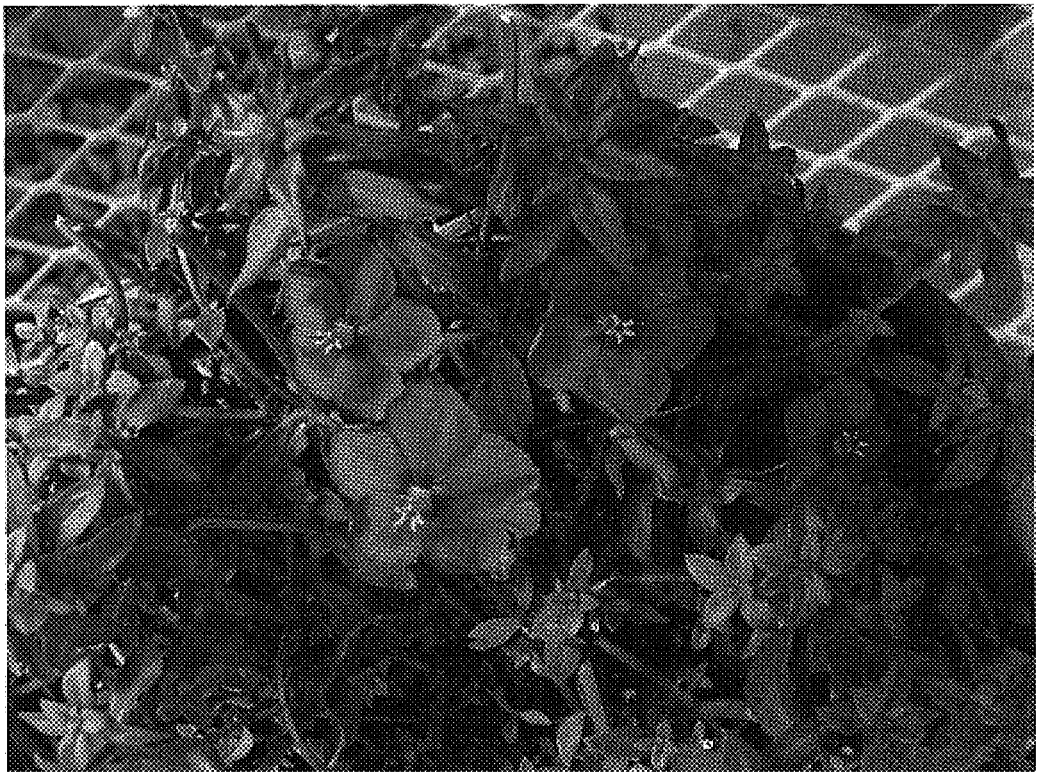

* * * * *